(12) United States Patent
Fuyuki

(10) Patent No.: US 7,601,941 B2
(45) Date of Patent: Oct. 13, 2009

(54) METHOD AND APPARATUS FOR EVALUATING SOLAR CELL AND USE THEREOF

(75) Inventor: Takashi Fuyuki, Ikoma (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 164 days.

(21) Appl. No.: 11/791,761

(22) PCT Filed: Nov. 29, 2005

(86) PCT No.: PCT/JP2005/021912

§ 371 (c)(1),
(2), (4) Date: May 29, 2007

(87) PCT Pub. No.: WO2006/059615

PCT Pub. Date: Jun. 8, 2006

(65) Prior Publication Data

US 2008/0088829 A1    Apr. 17, 2008

(30) Foreign Application Priority Data

Nov. 30, 2004    (JP) .............................. 2004-347084

(51) Int. Cl.
G01J 1/00 (2006.01)
G01M 11/00 (2006.01)
H01L 21/06 (2006.01)
H01L 31/04 (2006.01)

(52) U.S. Cl. .............................. 250/214 R; 250/338.1; 250/339.14; 250/341.4; 324/501; 324/752

(58) Field of Classification Search ............. 250/214 R, 250/252.1, 338.1, 339.14, 340, 341.14, 341.4; 356/230, 237.1; 324/501, 750, 752; 438/16, 438/17

See application file for complete search history.

(56) References Cited

U.S. PATENT DOCUMENTS 4,287,473 A * 9/1981 Sawyer ..................... 324/752
5,396,068 A * 3/1995 Bethea ..................... 250/330

(Continued)

FOREIGN PATENT DOCUMENTS

JP    09-266322    10/1997
JP    2002-272017    9/2002

OTHER PUBLICATIONS

International Search Report (PCT/ISA/210).

(Continued)

*Primary Examiner*—John R Lee
(74) *Attorney, Agent, or Firm*—Harness, Dickey & Pierce, PLC

(57) ABSTRACT

Disclosed is a method for evaluating the performance of a solar cell which comprises a silicon semiconductor as the main component. This method comprises a current introduction step for introducing a direct current into a solar cell element constituting the solar cell in the forward direction, and an emission sensing step for sensing emission characteristics of the light emitted from the solar cell element due to the current introduction step. By this method, the photoelectric conversion performance of a solar cell can be simply and accurately evaluated without requiring large-sized equipment.

14 Claims, 10 Drawing Sheets

U.S. PATENT DOCUMENTS

| | | | | |
|---|---|---|---|---|
| 6,670,820 B2* | 12/2003 | Stokes et al. | ............... | 324/767 |
| 6,674,064 B1* | 1/2004 | Chernyak et al. | ........ | 250/214.1 |
| 6,840,666 B2* | 1/2005 | Enachescu et al. | ............ | 374/5 |
| 6,946,858 B2* | 9/2005 | Matsuyama | ................ | 324/752 |

OTHER PUBLICATIONS

Honsberg et al. "Light Emission as a Solar Cell Analysis Technique". Solar Cells, vol. 20, No. 1, 1987, pp. 59-63.

Fuyuki et al. "Photographic Surveying of Minority Carrier Diffusion Length in Polycrystalline Silicon Solar Cells by Electroluminescence". Applied Physics Letters, vol. 86, No. 26, Jun. 27, 2005, pp. 262108-1 to 262108-3.

Fuyuki, T., et al., "Photographic surveying of minority carrier diffusion length in polycrystalline silicon solar cells by electroluminescence," Applied Physics Letters. Jun. 27, 2005. vol. 86, No. 26, pp. 262108-1, 262108-3.

Sakitani, N., et al., "Evaluation of Recombination Velocity at Grain Boundaries in Poly-Si Solar Cells with Laser Beam Induced Current," Solid State Phenomena. vol. 93 (2003), pp. 351-354.

Takamoto, Tatsuya, et al., "Study on Performance Uniformity of InGaP/GaAs Tandem Solar Cells by Using Photoluminescence and Electroluminescence Techniques," presented at the 14th European Photovoltaic Solar Energy Conference, Jun. 30-Jul. 4, 1997 in Barcelona, Spain, pp. 1-4.

Fuyuki, Takashi, et al., "Analytic findings in the electroluminescence characterization of crystalline silicon solar cells," Journal of Applied Physics 101, 023711 (2007) pp. 023711-1-023711-5.

Green, Martin A., et al., "Efficient silicon light-emitting diodes," NATURE vol. 412, Aug. 23, 2001, pp. 805-808.

Wang, Keda, et al., "Electroluminescence and forward bias current in *p-i-n* and *p-b-i-n a*-Si:H solar cells," J. Appl. Phys. 73 (9), May 1, 1993, pp. 4567-4570.

Tajima, Michio, et al., "Luminescence Characterization of Silicon Solar Cells," Extended Abstract of 38th meeting (Spring Meeting in 1991) of the Japan Society of Applied Physics and Related Societies (Tokai University, Shonan Campus), vol. 2, No. 29aSx12, p. 648 (1991).

\* cited by examiner

F I G. 1
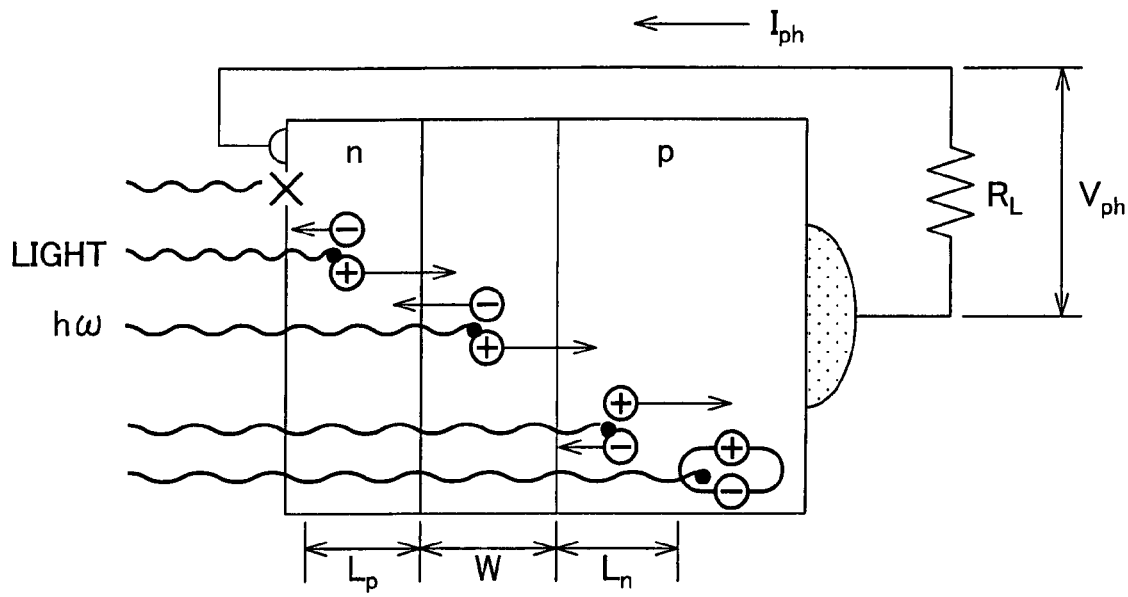
F I G. 2
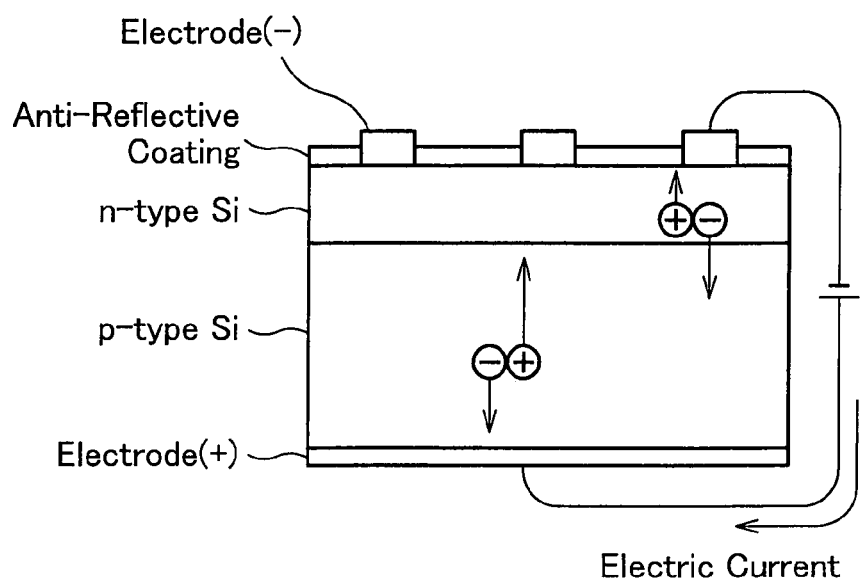

F I G. 6
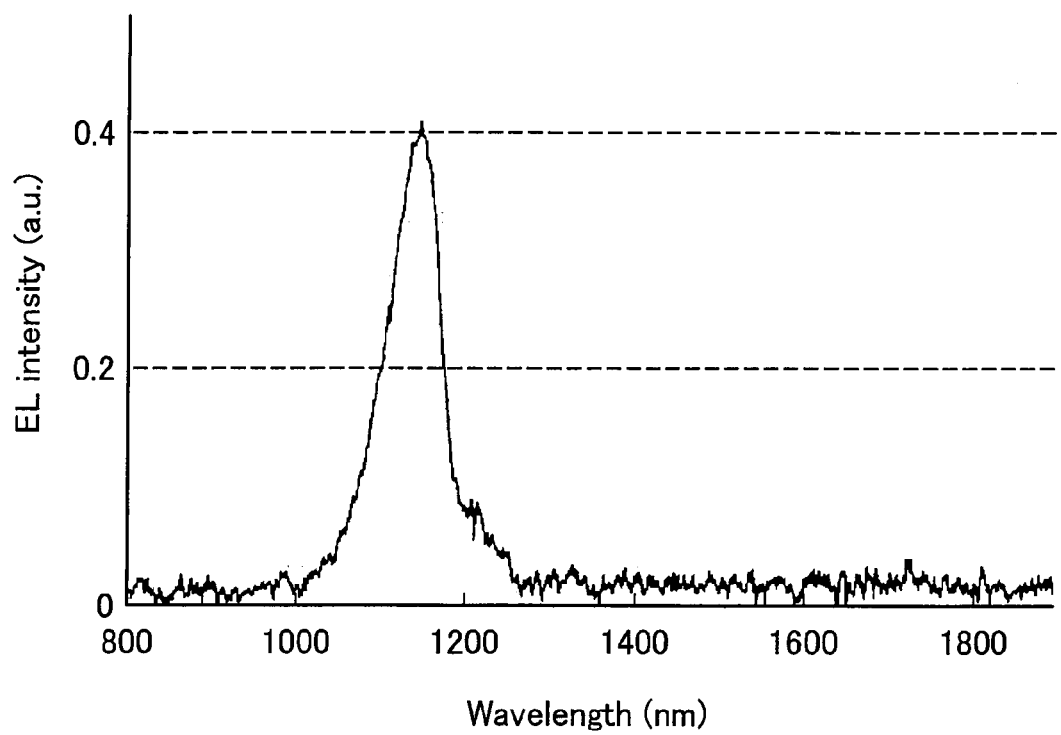

METHOD AND APPARATUS FOR EVALUATING SOLAR CELL AND USE THEREOF

TECHNICAL FIELD

The present invention relates to a method and apparatus for evaluating a solar cell easily and accurately in terms of a photoelectric conversion performance without using a large-sized detecting apparatus or the like, and use thereof. Especially, the present invention relates to a method and apparatus for evaluating a solar cell easily and accurately in terms of a photoelectric converting performance by passing an electric current through solar cell elements (e.g., a solar cell module, solar cell panel, or solar cell element per se) constituting the solar cell, and analyzing a light characteristics due to the electric current passage.

BACKGROUND ART

For keeping the environment of the earth, use of solar energy is getting popular. Albeit solar cell modules including solar cell elements in which a plurality of solar cells are linked are implemented on more and more roofs or walls of ordinary buildings and houses, high cost of the solar cell made of Si (silicon) or the like hinders wide use of the solar cell.

One cause of the high cost of the solar cell is a need of a step of evaluating an output characteristics thereof regarding an output thereof made when sun light is irradiated on the solar cell module, that is a need of step of evaluating characteristics of the solar cell module. The step of evaluating the output characteristics of the solar cell module measures an important item in post-production inspection of the solar cell module and in research and development of solar cells.

In general, it is difficult to evaluate the output characteristics of the solar cell module by irradiating sun light directly on the solar cells, for example, because intensity of the sun light varies depending on weather. On this account, the step of evaluating the output characteristics of the solar cell module generally uses a so-called solar simulator, that is, a light source typically using Xe (xenon) lamp or halogen lamp as a light source for evaluating the output characteristics of the solar cells, instead of actual sun light (see Patent Citation 1 for example). Moreover, a method for evaluating the solar cells by using an LED as a light source instead of the Xe lamp or halogen lamp (see Patent Citation 2 for example) has been developed.

Meanwhile, so-called EBIC (Electron Beam Induced Current) and LBIC (Laser Beam Induced Current), that is, methods for measuring a current or voltage induced by using an electron beam or laser beam and thereby analyzing diffusion length of minority carriers and defects (grain boundary/transgranular), are widely used as alternative methods for evaluating the performance of the solar cells by using the solar simulator.

By the EBIC or LBIC, it is possible to measure and evaluate a degree of an elective activity or diffusion length of the minority carriers in solar cells locally. It is possible to evaluate conversion efficiency and quality of the solar cell based on the result thereof (Non-Patent Citation 1).

Furthermore, because a solar cell has a pn junction and a structure similar to that of a light emitting diode (LED). A solar cell element (InGaP/GaAs) including a gallium arsenide monocrystalline semiconductor, which is generally using in the LED, has been developed. Techniques for evaluating such a solar cell element including gallium arsenide monocrystalline semiconductor have been reported. The evaluation is carried out by applying on the solar cell element a bias in a forwarding direction so as to cause electroluminescence (EL) and observe the EL. In-plane Unevenness in an EL intensity due to uneven current density distribution and pn junction-leakage-causing defect are evaluated based on the observation. (For example, see Non-Patent Citations 2 and 3.)

[Patent Citation 1]
Japanese Unexamined Patent Application Publication, Tokukai, No. 2002-48704 (published on Feb. 15, 2002).

[Patent Citation 2]
Japanese Unexamined Patent Application Publication, Tokukai, No. 2004-281706 (published on Oct. 7, 2004).

[Non-Patent Citation 1]
N. Sakitani, et al., "Evaluation of Recombination Velocity at Grain Boundaries in Poly-Si Solar Cells with Laser Beam Induced Current" Solid State Phenomena Vol. 93 (2003), pp. 351-354

[Non-Patent Citation 2]
Tatsuya Takamoto, et al., "STUDY ON PERFORMANCE UNIFORMITY OF InGaP/GaAs TANDEM SOLAR CELLS BY USING PHOTOLUMINESCENCE AND ELECTROLUMINESCENCE TECHNIQUES", presented at the 14th European Photovoltaic Solar Energy Conference, 30 Jun.-4 Jul., 1997 in Barcelona, Spain

[Non-Patent Citation 3]
Tatusya, TAKAMOTO, Thesis for a doctorate (engineering) "Research on Improvement of InGaP/GaAs tandem structure solar cell in efficiency and its property", Toyota Technological Institute, Postgraduate School of Engineering, submitted January, 1999.

The solar simulator and apparatuses for EBIC or LBIC are however, large in size and requires high equipment investment. Moreover, there is such a problem that the evaluation methods using these apparatus are actually complicated. That is, evaluation cost in the production cost of the solar cells has not been lowered due to high equipment cost of the measuring apparatuses for measuring and evaluating the performance of the solar cell element, and time-consuming measurement process.

Moreover, shipping inspection of solar cells by the solar simulator should measure an output current or output voltage of the whole solar cell module, thereby inspecting photoelectric conversion efficiency of the whole solar cell module. This cannot perform such a detailed analysis to find out which solar cell element at which portion of the solar cell module has a poor conversion efficiency.

Furthermore, the apparatus for EBIC or LBIC has many facility restrictions such as a need of an electron microscope for radiating the electron beam, or a multi-wavelength light source for radiating the laser beam. Therefore, it is not easy to perform this evaluation method for evaluating the solar cell module.

While the solar cell element made of a silicon-based material is most popular at present, a technique for evaluating the performance of such a solar cell element has not been developed albeit the technique for evaluating, by an EL method, the solar cell element made of monocrystals of InGaP/GaAs in terms of in-plane unevenness in EL intensity and in terms of the defect that will cause leakage in pn junction.

InGaP/GaAs has been generally used as a raw material for LED, and it has been a well known fact that it is easy to cause InGaP/GaAs to emit light by biasing InGaP/GaAs in the forwarding direction. Therefore, it has been relatively easy to arrive such a concept to evaluate the performance of the solar cell element by EL method. Silicon semiconductor, by contrast, has not been reported that it emits light under normal conditions while silicon semiconductor, even though it is an indirect transition semiconductor, emits light due to light emitting transition (caused by hot carrier etc.) or braking radiation under special conditions (such as being under low temperatures or under high electric field application, etc.) and there are reported a few cases that such light emission is utilized to perform property evaluation or performance evaluation. Therefore, silicon semiconductor has not been used as a light emitting material for LED or the like.

As described above, the light emitting characteristics of silicon semiconductor is not sufficient and silicon semiconductor is clearly different from GaAs in terms of its property. On this account, the knowledge regarding InGaP/GaAs cannot be directly applied to silicon semiconductor.

Furthermore, the knowledge regarding InGaP/GaAs disclosed in Non-Patent Citations 2 and 3 discuss about the solar cell element made of monocrystals of gallium arsenide semiconductor. Monocrystalline semiconductors have such an electron property that in-plane distribution does not occur and that makes it possible to form elements thereof with uniform property. Because of this, an element made of a monocrystalline semiconductor can be evaluated with no particular difficulty. However, polycrystalline semiconductors have such an electron property that in-plane distribution occurs, and that makes it possible to form elements only with largely varied properties. Thus, the use of a polycrystalline semiconductor requires more accurate evaluation.

Therefore, there has been a demand for development of a method and apparatus for evaluating a solar cell, each of which make it possible to evaluate photoelectric conversion performance of a solar cell module easily and accurately, and use thereof. Especially, silicon polycrystalline solar cell has been rapidly advanced to practical use. There is an immediate demand for development of an evaluation method etc. to contribute to high performance thereof.

DISCLOSURE OF INVENTION

In view of the aforementioned problem, an object of the present invention is to provide a method and apparatus for evaluating a solar cell, which allow to evaluate a solar cell module in terms of its photoelectric conversion easily and accurately, without requiring a large-sized facility, and use thereof.

As a result of diligent studies to solve the problem, the inventor of the present invention found that luminescence could be observed under normal carrier introducing condition at room temperature when passing a forward current through monocrystalline and/or polycrystalline semiconductor silicon, and experimentally confirmed that emission intensity of the luminescence was in 1:1 proportion with distribution of a diffusion length of minority carriers, which is largely influential on a photoelectric conversion performance. The present invention was accomplished based on this finding and confirmation. The present invention was accomplished on such novel knowledge and encompasses the following inventions.

(1) A method for evaluating performance of the solar cell, comprising:

the current passing step of passing, in a forward direction, a direct current through a solar cell element constituting the solar cell; and the light detecting step of detecting a light characteristic of light emitted from the solar cell element by the current passing step, the solar cell element being made from silicon semiconductor as its main component.

(2) The method as set forth in (1), comprising:

the judging step of judging the performance by using, as an indicator, emission intensity among the light characteristic detected in the light detecting step, so as to judge the performance as good when the light intensity is greater than a predetermined value, and to judge the performance as bad when the light intensity is smaller than a predetermined value.

(3) The method as set forth in (1), further comprising:

the judging step including:

calculating a diffusion length of minority carriers from emission intensity among the light characteristic detected in the light detecting step; and judging the performance of the solar cell by using the diffusion length as an indicator.

(4) The method as set forth in any one of (1) to (3), wherein an intensity of the current to be passed in the current passing step is substantially equivalent to that of an operating current of the solar cell element.

(5) The method as set forth in (1), wherein:

the current passing step passes the current that is changed in its intensity;

the light detecting step detects how the light characteristic of the light emitted from the solar cell element is changed according to the change in the intensity of the current; and the method comprises the step of calculating out a diode factor of the solar cell element from the change in the intensity of the current and the change in the light characteristic.

(6) The method as set forth in any one of (1) to (5) wherein the silicon semiconductor is monocrystalline, polycrystalline, or amorphous.

(7) The method as set forth in any one of (1) to (6), wherein the light detecting step detects light of wavelengths in a range of 1000 nm to 1300 nm.

(8) An apparatus for evaluating photoelectric conversion performance of a solar cell, the apparatus comprising:

current passing means for passing, in a forward direction, a direct current through a solar cell element constituting the solar cell; and light detecting means for detecting a light characteristic of light emitted from the solar cell element by passing the current therethrough by the current passing means, and the solar cell element being made from silicon semiconductor as its main component.

(9) The apparatus as set forth in (8), comprising:

judging means for judging the performance by using, as an indicator, emission intensity among the light characteristic detected in the light detecting step, so as to judge the performance as good when the light intensity is greater than a predetermined value, and to judge the performance as bad when the light intensity is smaller than a predetermined value.

(10) The apparatus as set forth in (8), further comprising:

judging means for calculating a diffusion length of minority carriers from emission intensity among the light characteristic detected in the light detecting means, and judging the performance of the solar cell by using the diffusion length as an indicator.

(11) The apparatus as set forth in (8), wherein:

the current passing means passes the current that is changed in its intensity;

the light detecting means detects how the light characteristic of the light emitted from the solar cell element is changed according to the change in the intensity of the current; and the apparatus comprises calculating means for calculating out a diode factor of the solar cell element from the change in the intensity of the current and the change in the light characteristic.

(12) A method for performing maintenance of a solar cell, the method comprising:

an apparatus as set forth in any one of (8) to (11) evaluating the solar cell that is implemented on a construction;

a judging apparatus judging, based on a result of the evaluation of the solar cell, whether the solar cell has a solar cell element whose performance is below a predetermined value; and a replacement instructing apparatus instructing, via a communication network, a replacement party for the solar cell element, to replace the solar cell element whose performance is below the predetermined value.

(13) A system for performing maintenance of a solar cell, comprising:

an apparatus as set forth in any one of (8) to (11);

a judging apparatus for judging, based on a result of the evaluation performed by the apparatus, whether the solar cell has a solar cell element whose performance is below a predetermined value; and a replacement instructing apparatus for instructing, via a communication network, a replacement party for the solar cell element, to replace the solar cell element whose performance is below the predetermined value.

(14) A method for producing a solar cell, comprising, as one step thereof, a method as set forth in any one of (1) to (7).

Apart from the judging means in the apparatus for evaluating the solar cell, each functional block (e.g., the judging apparatus, replacement instructing apparatus) of the maintenance method and maintenance system may be realized by a computer. In this case, a control program for causing a computer to function as each mean thereby to realize the evaluating apparatus etc. by the computer, and a computer-readable recording medium storing the control program are also within the scope of the present invention.

According to the method and apparatus of the present invention for evaluating the solar cell, it is not necessary to use a large-sized facility due to the use of electroluminescence carried out by passing the forward current, compared with the conventional method and apparatus for evaluating the solar cell.

Furthermore, the method and apparatus of the present invention for evaluating the solar cell is advantageous over the conventional art, for example, in (i) it is not necessary to use a scanning probe (electron beam, laser), thus the measurement can be done easily, (ii) a large facility is not necessary, thus it is possible to observe and evaluate the solar cell as a product (as a product completed in the manufacturing factory or as a product implemented on a construction). Because of these and other advantages, it is also possible to establish a business model such as a maintenance method or a maintenance system in which a solar cell implemented on a construction is evaluated on a regular basis. The maintenance method and the maintenance system makes it possible to perform maintenance of the solar cell implemented on a construction, which has not been seldom carried out. Further, the maintenance method and the maintenance system make it possible to select a solar cell element whose performance is poor, instead of replacing the whole solar cell module. This attains high efficiency and low cost.

For a fuller understanding of the nature and advantages of the invention, reference should be made to the ensuing detailed description taken in conjunction with the accompanying drawings.

BRIEF DESCRIPTION OF DRAWINGS

FIG. 1 is a view schematically illustrating a basic structure and operation principle of a solar cell module.

FIG. 2 is a view schematically illustrating passage of forward current through a solar cell element.

FIG. 6 is a view illustrating the result of analysis of emission intensity (EL intensity) from the Si solar cell element, and wavelength of light emitted from a solar cell module when caused by passing the current through the Si solar cell element.

EXPLANATION OF LETTERS OR NUMERALS

Figure 3:
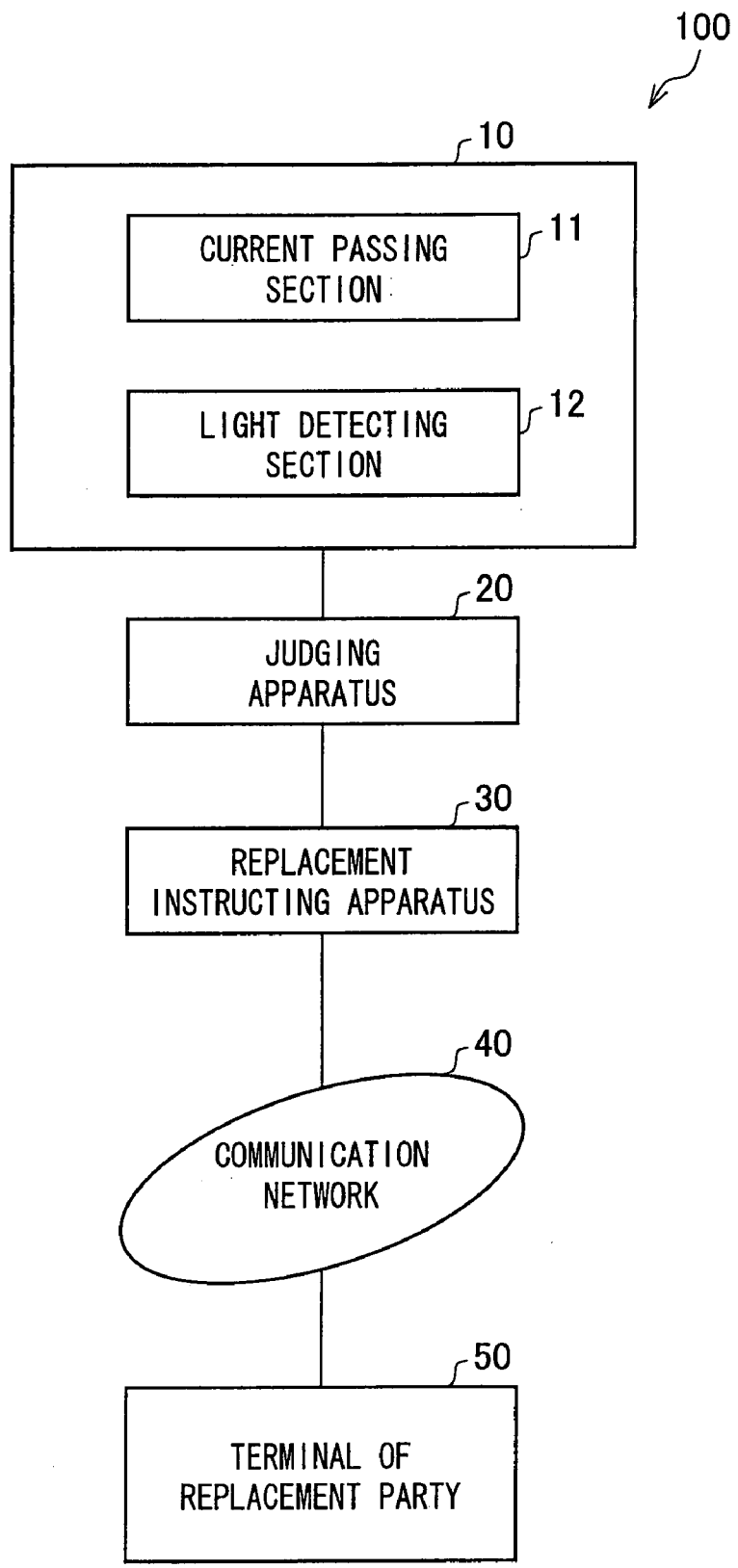
FIG. 3 is a view illustrating a functional block diagram schematically illustrating one example of a maintenance system according to a present embodiment.

10: Apparatus for Evaluation
11: Current Passing Section (Current Passing Means)
12: Light Detecting Section (Light Detecting Means)
20: Judging Apparatus (Judging Apparatus, Judging Means)
30: Replacement Instruction Apparatus
40: Communication Network
100: Maintenance System

BEST MODE FOR CARRYING OUT THE INVENTION

One embodiment of the present invention is described below.

<1. Method for Evaluating Solar Cell>

Referring to FIG. 1, a solar cell module is briefly described in terms of its basic structure and operation principle. For easy explanation, a solar cell element made from silicon semiconductor is described by way of example. In this Description, what is meant by the term "solar cell element" is a smallest constituent unit for generating an electric current on receiving light thereon due to photoconductive effect and/or photovoltaic effect. For example, the solar cell element is in a size of 10×10 cm to 15×15 cm. Moreover, what is meant by the term "solar cell module" is a module formed by linking a plurality of the solar cell elements. One example of the solar cell module is formed by linking 10 to 50 solar cell elements and is sized in the order of 0.5×0.5 m to 1×1 m. Moreover, in this Description, the term "solar cell module" encompasses "solar cell panels" that includes a plurality of the modules. Furthermore, the term "solar cell" is to mean any one or all of the solar cell element, solar cell module, and solar cell panel.

As described in FIG. 1, the solar cell element made from silicon semiconductor has such a structure that a thin n-type silicon layer (hereinafter, referred to as "n layer") is provided on a p-type silicon layer (hereinafter, referred to as "p layer"). (Even though it is not illustrated here, there is a P$^+$/n type solar cell element, and the present invention is also applicable thereto.) In FIG. 1, Lp is a diffusion length of holes, which are minority carriers in the n layer. Pn is a diffusion length of electrodes which are minority carriers in the p layer. W is a depletion layer width (a region in which an electric field exists without electrons and holes) formed by a pn junction. In short, the diffusion lengths are distances in which the minority carries formed by light can move (diffuse) before its recombination with majority carriers and consequent disappearance.

The light is radiated from above a surface of the n layer. The presence of many donors in the n layer shortens Lp. Thus, it is arranged such that the n layer is thin and most of light absorption is carried out in the p layer. Among electron-hole pairs generated by the light in the range of Ln from an edge of the depletion layer in FIG. 1, the electrons, which are the minority carriers, are diffused in the left direction and reach the depletion layer. Then, the electrons are moved to the n layer by the electric field in the depletion layer, and form a photo current. On the other hand, electrons from the electron-hole pairs formed by the light in a far distance from Ln and the holes, which are majority carriers, are recombined with each other to generate heat, whereby the electrons will not reach the depletion layer and contribute to the photo current.

This means that the longer diffusion length of the electrons, which are the minority carrier of the p layer attains better photoelectric conversion performance because the longer diffusion length of the electrons make it possible for electrons generated in deeper portion of the solar cell element to contribute to the current. In this way, the diffusion length of the minority carrier (electron) and the photoelectric conversion performance are closely related with each other in the solar cell element.

As a result of diligent studies, the inventor of the present invention found that passing a forward current through the solar cell element made from silicon conductor introduces electrons in the p layer where electrons are minority carriers, and the electrons thus introduced are recombined with holes in the p layer thereby causing light emission. Further diligent studies by the inventor revealed that, among the light characteristics of the solar cell element, an emission intensity of the emitted light and distribution of the diffusion length of the minority carrier are in 1:1 proportion. As a result, the inventor accomplished the present invention that makes it possible to easily and accurately evaluate the photoelectric conversion performance of the solar cell element by using, as an indicator, the light characteristics of the solar cell element that is caused to emit light by passing a current therethrough.

That is, a method according to the present invention for evaluation a solar cell, the method should at least include: the current passing step of passing, in a forward direction, a direct current through a solar cell element that constitute the solar cell (for example, a solar cell module or solar cell element itself); the emitted light detecting step of detecting light characteristics of light emitted from the solar cell element by the current passing step. Apart from that, the present invention is not particularly limited and may employ a conventionally known method etc. in terms of specific steps other than these steps, materials, conditions, device and equipment to use, etc.

Here, what is meant by the term "performance evaluation" in this Description is evaluation of the performance of the solar cell module or the solar cell element, which is a constituent of the solar cell module, in terms of photoconductive effect and/or photovoltaic effect. Moreover, the photoelectric conduction performance and the diffusion length of the minority carrier are closely related with each other as described above. Thus, the performance evaluation may be evaluation of the diffusion length of the minority carrier.

In the current passing step, the wording "passing the direct current in the forward direction" means to bias in the so-called forward direction, as illustrated in FIG. 2. The direct current is passed therethrough in the forward direction by externally applying a voltage which is positive (+) on the p-type region side and negative (−) on the negative region side of the pn junction.

In the current passing step, an apparatus for passing the current through the solar cell element may be a power supply or the like conventionally known, and is not particularly limited. For example, a general constant current source may be used as the apparatus for passing the current through the solar cell element.

In the emitted light detecting step, light detecting means conventionally known may be employed, which is capable of detecting light characteristics of the light emitted from the solar cell element. A light detecting means to be employed in the emitted light detecting step is not particularly limited in terms of specific configuration. For example, a conventionally known light detecting apparatus such as a CCD camera or the like may be used in the emitted light detecting step. Moreover, the detection of the light characteristics may be carried out by detecting the light characteristics for the whole solar cell module at once, or by detecting light characteristics for a particular portion of the solar cell module by using a small-sized light detecting apparatus. That is, there is no particular limitation on the light detecting step in terms of its specific method and the like, and a conventional technique may be employed as appropriate.

Moreover, the term "light characteristics" encompasses emission intensity of the emitted light, and spectral characteristics (emission intensity of each spectrum).

According to the method of the present invention for evaluating a solar cell, a whole solar cell module formed by linking solar cell elements in series can be evaluated in its performance by passing the current once therethrough. Once the current is applied, the current passes through all the solar cell elements constituting such a solar cell module thereby causing all the solar cell elements to emit light. In this case, the present invention may be arranged to measure an in-plane distribution of momentary luminance batchwise. More specifically, for example, this may be carried out by measuring a large area by 2-dimensional batchwise measurement or 1-dimensional line scanner, e.g., by using a CCD or the like. Note that the present invention is not limited to this. By detecting the light characteristics for the whole solar cell module by using a large-sized light detecting means or a line scanner for 1-dimensional scanning, it is possible to plainly find out which solar cell element at which portion of the solar cell module is low in its performance, and it is easy to evaluate it. Of course, it is possible to evaluate the solar cell elements individually.

Furthermore, the method of the present invention for evaluating the solar cell preferably include a judging step for evaluating the solar cell by using, as an indictor, an emission intensity among the detected light characteristics, the judging step judging the solar cell as good when the emission intensity is above a predetermined value, and the judging step judging the solar cell as poor when the emission intensity is below a predetermined value.

Here, the "predetermined value" can be arbitrarily set, and is not particularly limited. For example, the predetermined value may a so-called threshold below which no sufficient light electric conduction performance can be attained. As an alternative, the predetermined value may be a value that is worked out in advance by averaging the light characteristics of solar cell elements of good quality and/or of poor quality, which are manufactured in a manufacturing factory.

Moreover, the judging step may compare a numeric value of the emission intensity with the predetermined value. As an alternative, the judging step may use an apparatus for directly digitalizing the light characteristics as a light detecting apparatus for detecting the light characteristics such as a CCD camera, and compare a digitalized value of the light characteristics with the predetermined value. That is, it is sufficient that the judging step is a step of judging a light characteristic by comparing the measured light characteristics with a certain reference value. As to a method to employ specifically, the judging step may employ a conventionally known technique.

By including the judging step as described above, it is possible to evaluate the performance and/or quality easily and accurately to judge whether it is good or poor.

Figure 7A:
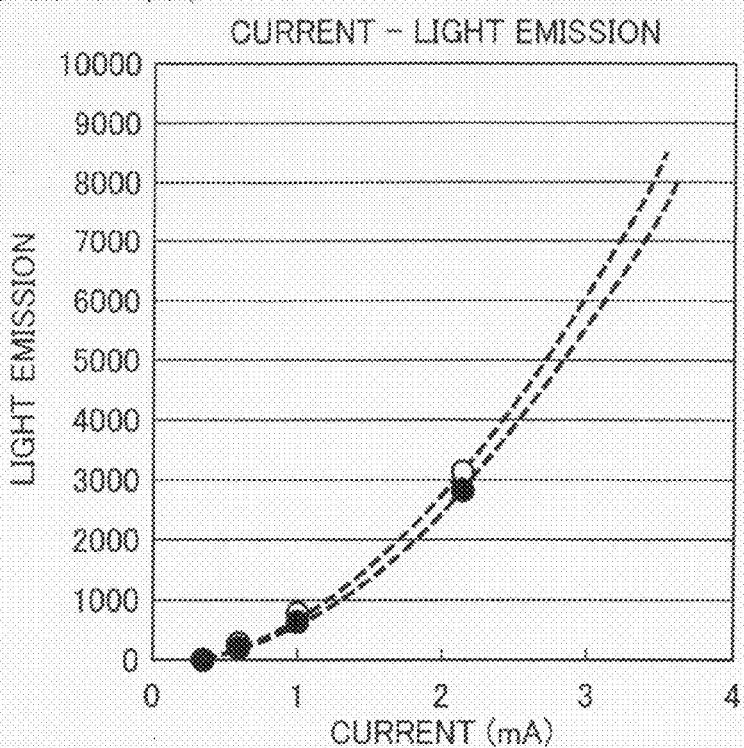
FIG. 7(a) is a view illustrating the result of analysis studying a relationship between an intensity of the current passing through the Si solar cell element, and the emission intensity.
Figure 7B:
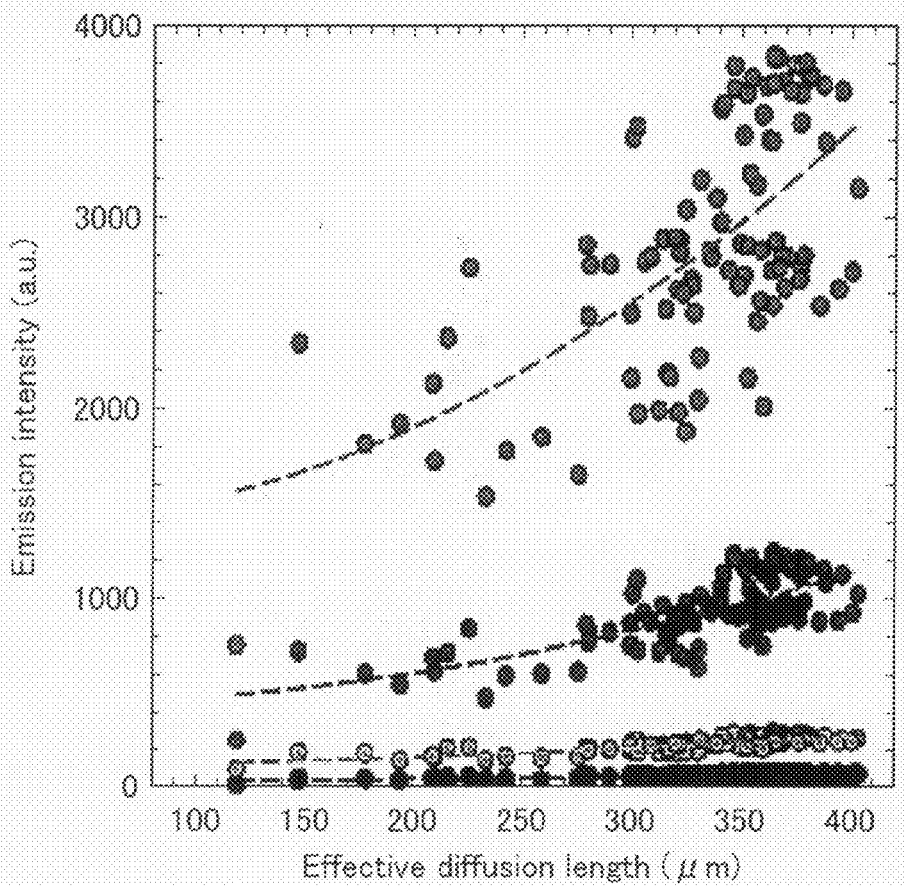
FIG. 7(b) is a view illustrating the result of analysis studying a relationship between a diffusion length and the emission intensity of the Si solar cell element.
Figure 11:
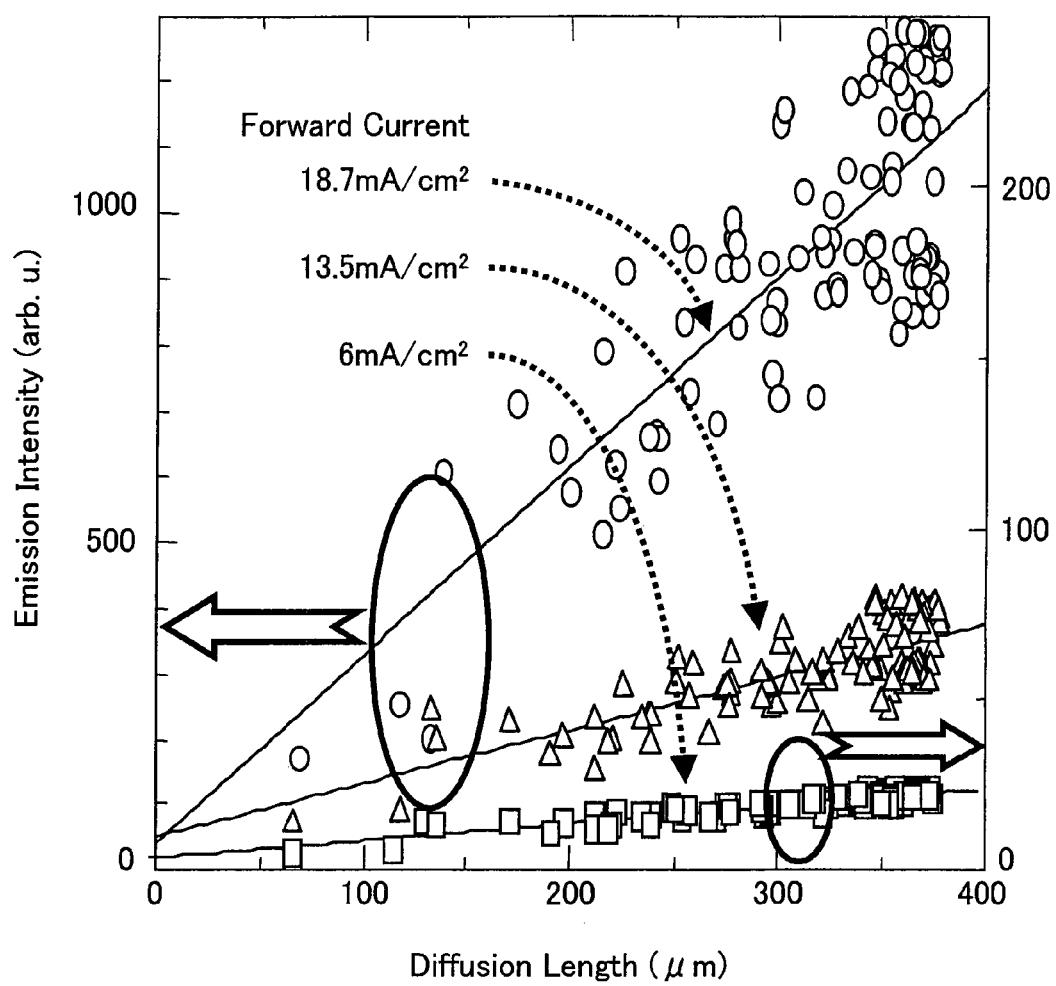
FIG. 11 is a view illustrating another graph showing the result of analysis on the relationship between the diffusion length and emission intensity of the Si solar cell element. The analysis especially examined the results for the forward currents of 6 mA/cm$^2$, 13.5 mA/cm$^2$, and 18.7 mA/cm$^2$, among the results of FIG. 7(b).

Furthermore, the method for evaluating the solar cell may include a judging step of evaluating the performance of the solar cell module by using, as an indicator, a diffusion length of the minority carrier, the diffusion length being worked out from the emission intensity of the light characteristics detected in the light detecting step. To describe more specifically, there is a correlation between the diffusion length of the minority carrier and a light characteristic (e.g., emission intensity), as illustrated in FIGS. 7(b) and 11 of examples later described.

Therefore, it is possible to evaluate the performance of the solar cell element based on that diffusion length of the minority carrier which is worked out from a light characteristic. One example of specific methods of working out the diffusion length of the minority carrier is to work out analogically from a graph plotting the light characteristic and the diffusion length of the minority carrier, as illustrated in FIG. 7(b) or FIG. 11 later described. Criterion of the diffusion length of the minority carrier depends on the structure of the element and cannot be specifically defined. However, a loner diffusion length of the minority carrier is preferable.

There is no particular limitation as to the solar cell element to be evaluated by the method for evaluating the solar cell. It is sufficient that the solar cell element is a solar cell element whose main component is a conventionally known semiconductor material. It is preferable that the solar cell element be made mainly from silicon semiconductor. In the present Description, the wording "be made mainly from" means that it may include any component or constituent other than the main component, as long as the main component is the silicon semiconductor.

Silicon conductor is an indirect semiconductor but emits light under specific conditions (under low temperature, under high electric field application, etc.). The light emission of the silicon conductor is due to light-emitting transition (caused by hot carrier, etc.) or braking light radiation, and has been utilized to evaluate property, or function. For example, an apparatus for evaluating Si integrated circuit has been on the market (marketed by Hamamatu photonics. K.K. etc.) However, silicon semiconductor, which is an indirect semiconductor, is not so suitable for electroluminescence. There has not been many reports that the silicon semiconductor emits light under normal conditions (conditions other than the specific conditions). Therefore, silicon semiconductor is not utilized for LED.

In this point, silicon semiconductor is largely distinguishable from GaAs. That is, GaAs is a material that can be suitably used for LED, and that easily causes electroluminescence by its nature. In short, GaAs and silicon semiconductor are different in property clearly. Thus, even a person skilled in the art cannot arrive at the direct use of the knowledge of GaAs to the silicon semiconductor.

Despite of the above, the inventor of the present invention diligently worked to find that the solar cell element made from silicon conductor that has been rarely reported that it emits light under normal conditions, emits light when a forward current is passed through the solar cell element, and that the emission intensity of the light thus emitted from the solar cell element is closely related with the diffusion length of the minority carrier. While this finding should be appreciated as a scientific discovery, the invention based on the finding is industrially applicable to sufficiently meet the requirements for being patentable.

The silicon semiconductor for the solar cell element is preferably monocrystalline, polycrystalline, or amorphous. Among them, it is especially preferable that the solar cell element include amorphous silicon semiconductor as its main component. It is difficult to attain even in-plane distribution in the solar cell element made from amorphous silicon semiconductor as its main component. Thus, in case of the solar cell element made from amorphous silicon semiconductor as its main component, it is very important to evaluate its quality and check its performance according to the method according to the present invention.

Moreover, as described in Examples later described, the solar cell element made mainly from monocrystalline and/or polycrystalline silicon semiconductor intensely emits light in a wavelength range of from 1000 nm to 1300 nm when the forward current is passed through the solar cell element. Therefore, the method of the present invention for evaluating the solar cell may be arranged such that the light detecting step detects the light in the region of from 1000 nm to 1300 nm especially. This arrangement makes it possible to more accurately evaluate the solar cell element made from silicon semiconductor.

Moreover, it is preferable in the current passing step that an intensity of the current to pass is substantially equivalent to that of an operating current of the solar electron element. Here, the "operating current of the solar cell element" is a current that would be actually generated by photoelectric conversion as a result of the radiation of sun light on the solar cell element to be evaluated. For example, the operating current of the solar cell element made from silicone semiconductor is in a range of 5 to 40 mN/cm$^2$, typically. The present invention, however, is not limited to this value, and the intensity of the current to pass may be appropriately varied depending on the material and composition of various types of solar cell element. Moreover, any rational values out of the above numerical range are included in the technical scope of the present invention, provided that the effect of the present invention can be attained with the value.

By performing the evaluation under actual operating conditions, it is possible to evaluate the performance more accurately.

Albeit the method of the present invention for evaluating the solar cell is described referring to the solar cell module assumed to form by linking a many number of solar cell elements in series, a solar cell module formed by linking a many number of solar cell elements in parallel can be evaluated in such a manner that each portion of the solar cell module in which the solar cell elements are linked in series is evaluated individually.

The present invention may be arranged such that, for example, spectrum distribution measurement using a band pass filter or the like, or detailed spectrum measurement using a spectrometer may be carried out, apart from directly measuring the luminescence intensity by using, for example, a CCD camera after the forward current is passed through the solar cell element, and then results of these measurements are analyzed in a comprehensive manner. Especially, comprehensive analysis with absolute measurement of the diffusion length at a multi-wavelength spectrum sensitivity makes it possible to analyze distribution of the absolute values. In this case, the present invention is characterized in not using probe light, compared with a conventional art.

As described above, the method of the present invention for evaluating the solar cell makes it possible to evaluate the photoelectric conversion performance of the solar cell element easily and accurately without requiring a large-sized facility compared with the conventional method for evaluating the solar cell. More specifically, the method and apparatus according to the present invention for evaluating the solar cell utilize the electroluminescence in which the forward current is passed through. Thus, the method and apparatus according to the present invention are advantageous over the conventional art, for example, in (i) it is not necessary to use a scanning probe (electron beam, laser), thus the measurement can be done easily, (ii) a large facility is not necessary, thus it is possible to observe and evaluate the solar cell as a product (as a product completed in the manufacturing factory or as a product implemented on a construction), (iii) it is possible to evaluate the solar cell under actual operation condition (the condition under the sun light radiation is equivalent to passage of a current of 5 to 40 mA/cm$^2$), (iv) it is possible to perform more detailed physical analysis by spectrum analysis, (v) and the like.

Furthermore, the method and apparatus according to the present invention can easily further include light analysis using backward voltage or under high electric field application. This makes it possible to integrally evaluate the property of the minority carriers and the performance of the element due to the property of the minority carriers.

Moreover, the method according to the present invention for evaluating the solar cell may be arranged such that the current passing step includes changing the intensity of the current to be passed through and the light detecting step includes detecting how the light characteristic of the light from the solar cell element is changed according to the change in the intensity of the current, and the method further includes calculating a diode factor of the solar cell element from the change in the intensity of the current and the change in the light characteristic.

In this arrangement, it is preferable that a range of the change in the intensity of the current be within the actual operation conditions (for example, in a range of 5 to 40 mA/cm$^2$).

In this method, a specific method for calculating the diode factor is plotting the change in the intensity of the current (current density [mA/cm$^2$]) against the light characteristic (e.g., the emission intensity of the light, or the like) to draw a logarithmic graph (whose x axis is the change in the intensity of the current, and y axis is the change in the light characteristic). In this case, the gradient of the graph is the diode factor of the solar cell element.

It is known that the diode factor closer to "1," indicates formation of more ideal pn junction and is more advantageous in energy conversion efficiency. Thus, it is possible to judge that the performance of the solar cell element is good when the gradient of the graph is close to "1". Meanwhile it is possible to judge that the performance is poor when the gradient is increased from "1" (i.e., it get greater than "1"). That is, the evaluation method may further include evaluating the performance of the solar cell referring to whether the diode factor is close to "1" or not. In the above explanation, the ideal "diffusion current" component is "1", and the gradient increases when another component (recombining current component or the like) is mixed in. For example, the gradient becomes "2" when the mixing component is the recombining current.

Moreover, it was confirmed experimentally as described in the later-described Example that a greater emission intensity of the light got the gradient of the graph closer to "1". Moreover, it was confirmed that the diffusion current became dominant and thereby the gradient became substantially "1" when the solar cell element was made from monocrystalline silicon semiconductor, and that the influence from the other current components became greater when the solar cell element was made from polycrystalline silicon semiconductor.

Moreover, the method of the present invention for evaluating the solar cell may adopt a method other than these described above, in order to compare the measured value with a reference sample so as to judge whether the performance is good or poor. More specifically, for example, the method of the present invention for evaluating the solar cell may be carried out with the reference sample so as to obtain the result of evaluation of the reference sample, and then compare, with the result of evaluation of the reference sample, the result of the evaluation of the solar cell to be evaluated. This makes it possible to easily and surely evaluate the performance of the solar cell to be evaluated.

Moreover, the evaluation method according to the present invention can evaluate quantitatively as well as qualitatively. For example, the evaluation method according to the present invention can evaluate the performance of solar cell qualitatively by checking whether the emission intensity of the light is strong or weak. Meanwhile, the evaluation method according to the present invention can evaluate the performance of solar cell quantitatively by digitalizing the light characteristic of the solar cell element, and accurately analyzing the numerical information and positional information of the solar cell element. As to specific methods for such quantitative evaluation, a person skilled in the art should be able to easily implement an appropriate one based on the content of the present Description and the technical common sense as of the filing of the present application.

<2. Apparatus for Evaluating Solar Cell>

The apparatus of the present invention for evaluating the solar cell is an apparatus for evaluating the solar cell in terms of the photoelectric conversion performance thereof. It is sufficient that the apparatus include a current passing section (current passing means) for passing a direct current in the forward direction through the solar cell element constituting the solar cell, and light detecting means for detecting the light characteristic of the light emitted from the solar cell element by the passage of the current by the current passing section. The apparatus is not particularly limited in terms of other specific arrangement, size, shape, etc.

The current passing section is not particularly limited in terms of its specific arrangement etc., provided that it can apply a so-called direct bias on the solar cell element in order to pass the direct current therethrough in the forward direction. In the other words, the current passing means should be a means for carrying out the "current passing step" described in the item <1>. For example, the current passing means may be a conventionally known constant current source, constant voltage source, or the like.

Moreover, it is preferable that the current passing section pass, through the solar cell element, a current substantially equivalent to the operating current of the solar cell element.

The light detecting section is not particularly limited in terms of its specific arrangement etc., provided that the light detecting section is a means for detecting the light characteristic of the light emitted from the solar cell element when the forward bias is applied on the solar cell element. That is, the light detecting section should be a means for carrying out the "light detecting step" described in the item <1>. For example, a conventionally known light detector such as CCD camera or image intensifier may be suitably used. The term "light characteristics" used here means the same as the term used above.

In the other words, the apparatus of the present invention for evaluating the solar cell is an apparatus for carrying out "the method for evaluating the solar cell" described in item <1> above.

The apparatus of the present invention for evaluating the solar cell is not particularly limited in terms of what it evaluates. Thus, the apparatus of the present invention for evaluating the solar cell is applicable to general solar cells made from semiconductors. Of all, it is preferable that the apparatus of the present invention be used to evaluate a solar cell including silicon semiconductor as its main component. In the case of the solar cell element in which silicon semiconductor is used, emission of light especially in a range of 1000 nm to 1300 nm is observed. In this case, therefore, it is preferable that the light detecting section be capable of detecting the light in this wavelength region (near-infrared region).

Furthermore, the apparatus of the present invention for evaluating the solar cell preferably include a judging section judging means) for evaluating the solar cell by using, as an indictor, a emission intensity among the detected light characteristics, the judging section judging the solar cell as good when the emission intensity is above a predetermined value, and the judging section judging the solar cell as poor when the emission intensity is below a predetermined value. The judging section is not particularly limited in terms of its specific arrangement, provided that it can perform the "judging step" described in item <1>. For example, an arithmetic unit of a computer, or the like conventionally known may be the judging section suitably. Note the term "predetermined value" means the same as that used in item <1>. So, its explanation is omitted here.

Moreover, the apparatus of the present invention for evaluating the solar cell may be provided with a scanning section (scanning means) that is a system capable of performing 2-dimensional scanning, in addition to 1-dimensional scanning system, such as line scanner. With an apparatus of the present invention provided with such a scanning section a whole large-sized solar cell module including many solar cell element can be evaluated while being scanned. The scanning section may be included in the apparatus for evaluating or provided to the solar cell element to be evaluated. Meanwhile, it is possible to perform the evaluation without scanning. For example, the whole solar cell module may be evaluated at once by observing from above the solar cell element, or may be evaluated only partially.

Moreover, the apparatus of the present invention for evaluating the solar cell may further include a judging section (judging means) for calculating out a diffusion length of the minority carriers from the emission intensity among the characteristics detected by the light detecting section, and evaluating the performance of the solar cell module by using the diffusion length as an indicator. In the other words, the judging section is a judging means for performing the judging method described in item <1>. See item <1> for what this means performs specifically.

Moreover, the apparatus of the present invention for evaluating the solar cell may be arranged such that the current passing section changes the intensity of the current to be passed through, the light detecting section detects how the light characteristic of the light emitted from the solar cell element is changed according to the change in the intensity of the current caused by the current passing section, and the apparatus includes a calculating section (calculating means) for calculating a diode factor of the solar cell factor from the change in the current and the change in the light characteristic. Again, the calculating section should be a calculating means for performing the evaluating method described in item <1>, and an arithmetic apparatus conventionally known or the like may be adopted suitably. See item <1> for what the calculating section performs specifically. In the other words, the evaluating apparatus may include the evaluation section for evaluating the performance of the solar cell referring whether the diode factor is close to "1" or not.

Needless to say, the description regarding the method of the present invention for evaluating the solar cell in item <1> can be referred for and applied to the apparatus for evaluating the solar cell in terms of matters other than these described above.

Figure 10:
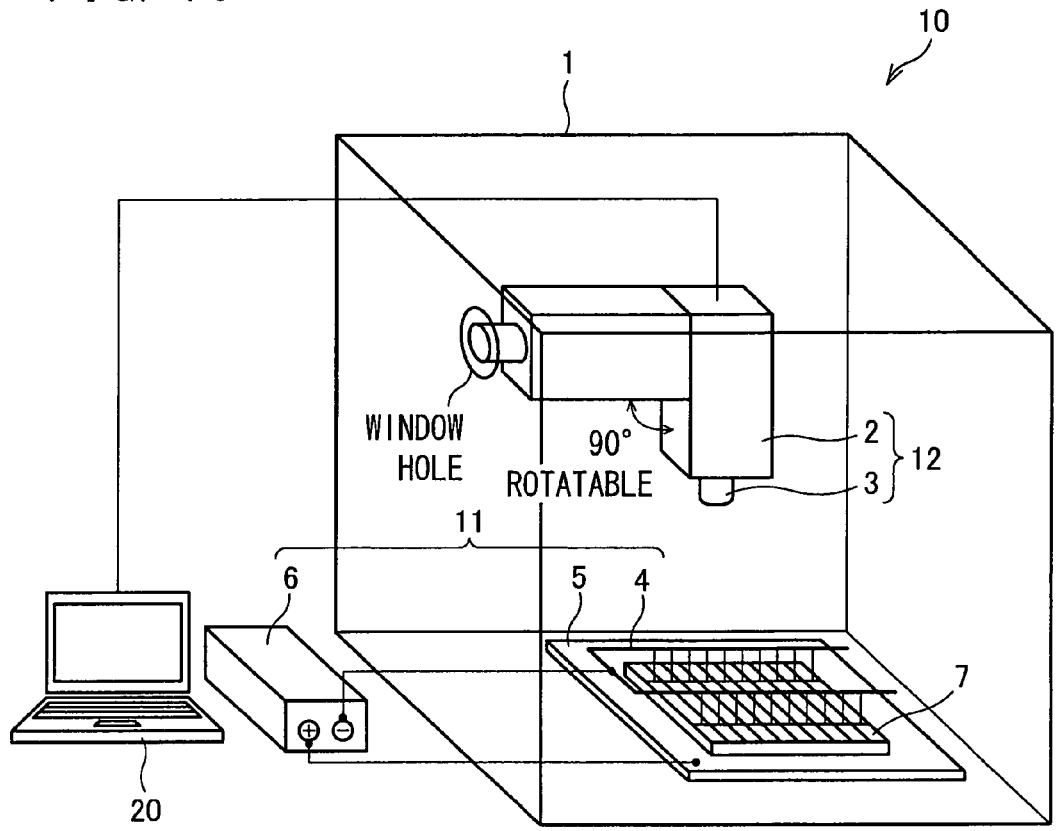
FIG. 10 is a view schematically illustrating an apparatus according to the present embodiment for evaluating a solar cell.

Next, one embodiment of the apparatus of the present invention for evaluating the solar cell is described below referring to FIG. 10. As illustrated in FIG. 10, an evaluating apparatus 10 according to the present embodiment for evaluating a solar cell includes a black box 1, a light detecting section 12, a comb-shaped probe 4, a copper plate 5, a direct current power supply 6, and a judging section 20. Moreover, a solar cell element 7 is to be evaluated here. Instead of the solar cell element 7, a module formed by linking a plurality of solar cell elements may be evaluated here.

The black box 1 is provided to from a dark condition for easy detection of the light characteristic of the solar cell element 7. The black box 1 has a window hole that is utilized in evaluating a solar cell module or panel that is set up in a perpendicular direction.

The light detecting section 12 functions as light detecting means including a CCD camera, and includes a cooled CCD (−50° C.) 2 and a lens 3. The light detecting section 12 is 90° rotatable to make it possible to evaluate the solar cell module that is set up in the perpendicular direction. Moreover, the lens may be a normal lens or zoom lens.

Moreover, in a case in which a cell (solar cell element) constituting solar cell elements 7 in different sizes are evaluated by using a CCD camera as the light detecting section 12, it is possible to use a CCD camera having the following capabilities shown in Table 1.

TABLE 1

CCD Camera
~For Picturing cells in different sizes~
Effective Element Size: 12.29 mm Normal Picturing Mode
Lens Capable of picturing the whole by picturing cell by cell.
Picturing Ranges: approx. 15, 25, 110, 160, 210 mm
Zooming Capable of zooming each cell
Minimum Picturing Range: 0.1 mm
Maximum Picturing Range: 210 mm
Movable in X and Y axes Capable of moving in X and Y-axis directions while zooming
Maximum Movable Ranges: approx. 210 mm
Module Picturing Mode
90° Rotation Capable of Picturing Module (1200 mm × 800 mm)
Distance between Module and Lens: approx. 3 m
Pictures Module placed out of Black Box.

More specifically, in the normal picturing mode, the picturing is carried out with the CCD camera positioned to be above the solar cell element as illustrated in FIG. 10. Meanwhile, in the module picturing mode, the solar cell module placed out of the black box 1, and the CCD camera is rotated 90° to picture and measure the solar cell module.

The sizes (cell sizes) of the solar cell element 7 to be evaluated in the normal picturing mode may be, for example, approximately 10, 20, 100, 150, 160, or 200 mm □ in dimension, and 0.3 mm or less in thickness.

Moreover, in the present embodiment, it is preferable that the distance between the lens 3 of the light detecting section 12 and the solar cell element 7 be set to be 150 mm or more but 400 mm or less, and that the light detecting section 12 be movable up and down in the distance between the light detecting section 12 and the solar cell element 7.

The comb-shaped probe 4 is surface contacts for applying the current on the solar cell element 7. The comb-shaped probe 4 includes a pair of a comb-shaped probes, as illustrated above. One tooth of the comb shape corresponds to one electrode of the solar cell element constituting the solar cell element 7. The probe with a comb-shaped structure can apply the current evenly on the solar cell element 7, and thus is preferable.

Especially, the comb-shaped probes for 100, 150, and 200 mm □ cells may be arranged to be different in a length and an electrode-electrode width of each pass bar electrode. For example, a pair of comb-shaped probes made by Atto System Corp. In this case, it is preferable that a distance between the two comb-shaped probes be adjustable. Furthermore, there is no particular limitation as to the distance between the "tooth" of the comb-shaped probes. For example, the distance between the "tooth" of the comb-shaped probes may be 9 mm. Moreover, the teeth of the comb-shaped probes may be 1 mm in width. Moreover, it is preferable to use one comb-shaped probe per one electrode.

For the solar cell element of 10 or 20 mm □, it may be arranged such that a probe from a positioner is used instead of using the comb-shaped probe.

Moreover, the copper plate 5 functions as a reverse contact. For example, the copper plate 5 may be a cold-plated copper plate. In this case, it is preferable to suck the solar cell element 7 overall. To encounter a consequent change in the cell size, square drains centered at the same center may be provided so as to perform the suction more stably. Dimensionwise, the drains may be, for example, 8 mm □, 18 mm □, 98 mm □, 148 mm □, and 198 mm □. Moreover, it is preferable to provide a temperature sensor and a cooling apparatus. This can make it possible to keep a temperature of the solar cell element so as to improve accuracy in the measurement and evaluation.

The direct current power supply 6 may be a normal DC power supply (1 mA to 50 A). The voltage may be in the order of 5V for evaluating the solar cell element or solar cell element. However, a voltage in the order of 100V is preferable for evaluating the solar cell module.

Moreover, the comb-shaped probe 4, copper plate 5, and the direct current power supply 6 functions as a current passing section 11. The comb-shaped probe 4 is connected to the negative side of the direct current power supply 6 and the copper plate 5 is connected to the positive side thereof.

The judging section 20 functions as the judging means for evaluating the performance of the solar cell element 7. In the present embodiment, an image processor is employed as the judging section 20. There is no particular limitation as to software to use, provided that the object of the present invention can achieved. The following is one preferable example of a structure of the software.

Capable of storing a 8-bit image ($2^8$=256 gray scales) or 16-bit image ($2^{16}$=65536 gray scales).

Capable of acquiring and storing luminance profile data of an area selected on a screen after detecting (picturing) the light characteristics of the solar cell element.

Capable of dealing with spectrum.

Capable of acquiring highly-sensitive image (image intensifier camera), e.g., capable of measuring emission at a reverse current application.

Furthermore, it is preferable to have the following arrangements.

improved in that an image obtained from data read by a spreadsheet software is rotated 90° to the pictured image.

Capable of easily switching to a beginning mode.

Programmed to automatically create a histogram of the emission intensity of the light.

Automatically measures a length and weight of a portion having low emission intensity of the light (i.e. a dark portion). Automatically measures dark portions of 1 cm or greater in size.

Calculates an average of the intensities of the light in a selected range (preferably being capable of measuring an average of the intensities with grid portions omitted).

Inside the black box 1, the light detecting section 12, the comb-shaped probe 4, the copper plate 5, and the solar cell element 7 are disposed. The light detecting section 12 is positioned to be able to detect the light characteristics of the solar cell element 7. In the present embodiment, the light detecting section 12 is disposed above the solar cell element 7.

An evaluation operation of the evaluating apparatus 10 for evaluating the solar cell is described here. To begin with, the current passing section 11 passes a current through the solar cell elements constituting the solar cell element 7. Accordingly the solar cell element emits light. The light detecting section 12 detects the light characteristic (emission intensity in the case of the present embodiment) of the solar cell element. The light detecting section 12 and the judging section 20 are connected with each other so as to send to the judging section 20 the result of the detection obtained by the light detecting section 12. Finally, the judging section 20 evaluates the performance of the solar cell element constituting the solar cell element 7 from the result of the detection.

As described above, it is possible to easily and surely perform the method for evaluating the solar cell described in item <1>, according to the apparatus of the present invention for evaluating the solar cell. In this case, a large-sized and complicated apparatus like the conventional evaluating apparatus is not required, but it is possible to evaluate the performance of the solar cell element accurately with a simple apparatus.

It should be noted that the present invention is not limited to the above description in which the apparatus and method for evaluating the solar cell element and the solar cell element are explained. The present invention is also applicable to evaluation of a solar cell panel formed by linking a plurality of the solar cell modules. In this case, the intensity of the current to apply, voltage, the shape of the probe, etc. can be modified if necessary. For example, it may be arranged such that the forward current is equivalent to a total current of currents in a range of 1 to 80 [mA/cm$^2$] per solar cell element. Moreover, a dark room may be used in replacement of the black box according to the size of the solar cell module. Moreover, as described above, the light detecting section 12 in FIG. 10 may be rotated 90° to picture a solar cell module that is set up in a perpendicular direction.

<3. Usage>

As described above, the method and apparatus of the present invention for evaluating the solar cell do not need a large-sized facility and can evaluate the performance of the photoelectric conduction performance the solar cell module easily and accurately, compared with the conventional method and apparatus for evaluating the solar cell.

Furthermore, it is possible to establish a business model such as a maintenance method and a maintenance system for regularly evaluating a solar cell implemented on a construction, because, for example, the method and apparatus of the present invention for evaluating the solar cell do not need, e.g., a scanning probe (electron beam, laser) and thus are able to perform easier measurement, compared with the conventional art. Moreover, the lack of the need of the large-sized facility makes it possible to observe and evaluate the solar cell as a product (as a product completed in the manufacturing factory or as a product implemented on a construction). Because of these and other advantages, it is possible to establish a business model such as a maintenance method or a maintenance system in which a solar cell implemented on a construction is evaluated on a regular basis.

That is, the present invention encompasses a method for performing maintenance of a solar cell, the method including the above-described evaluating apparatus performing evaluating of a solar cell module implemented on a construction, the judging means judging, based on a result of the evaluation on the solar cell module, whether or not the solar cell module has a solar cell element whose performance is blow a predetermined value, and replacement instructing means instructing, via a communication network, a solar-cell-element-replacing party to replace the solar cell element whose performance is blow the predetermined value.

Furthermore, the present invention encompasses a maintenance system for performing the maintenance method. The maintenance system according to the present invention at least includes the evaluation apparatus as described above, the judging apparatus for judging, based on a result of the evaluation on the solar cell module, whether or not the solar cell module has a solar cell element whose performance is blow a predetermined value, and a replacement instructing apparatus for instructing, via a communication network, a solar-cell-element-replacing party to replace the solar cell element whose performance is blow the predetermined value.

In the present Description, what is meant by the wording "solar cell module implemented on a construction" is a solar cell module that is already implemented on a construction such as residential facilities such as living houses, condominiums etc., business facilities such as shopping malls, office buildings, etc., or the like. For example, extruded from the "solar cell module implemented on a construction" is a solar cell that is being produced or is just produced in the manufacturing factory of the solar cell module, and that is not implemented on any construction.

FIG. 3 illustrates a functional block diagram schematically illustrating one example of the maintenance system according to the present embodiment. As illustrated in FIG. 3, a maintenance system 100 according to the present invention includes an evaluating apparatus 10, a judging apparatus 20, and a replacement instructing apparatus 30. The evaluating apparatus 10 includes a current passing section 11, and a light detecting section 12. The replacement instructing apparatus 30 is connected to a terminal 50 of a replacement party via the communication network 40. The communication network 40 and/or the terminal 50 of the replacement party may be included in the maintenance system or may be a given external network or a given terminal.

The current passing section 11 functions as the current passing means and performs the current passing step. The light detecting section 11 functions as the light detecting means and performs the light detecting step.

The judging apparatus 20 has a function of judging, based on the result of the evaluation performed by the evaluating apparatus, whether or not the solar cell module implemented on the construction has a solar cell element whose performance is below the predetermined value. The judging apparatus may be a conventionally known arithmetic unit such as a computer, or the like.

The replacement instructing apparatus 30 has a function of instructing, via the communication network, the replacement party for the solar cell element to replace the solar cell element whose performance is below the predetermined value.

Needless to say, one computer may function as the judging apparatus and the replacement instructing apparatus, while the present embodiment is arranged such that the judging apparatus 20 and the replacement instructing apparatus 30 are individual apparatuses.

Moreover, the communication network 40 may be a wired leased line or a communication line such as the Internet or the like. Moreover, the communication network 40 may be a network using a portable phone line or a wireless line.

The terminal 50 of the replacement party may be any terminal, provided that it can recognize the replacement instruction from the replacement instructing apparatus 30. It is preferable that the terminal 50 be provided with a display section (e.g., a display such as CRT or LCD), or an output section (e.g., a printer).

Figure 4:
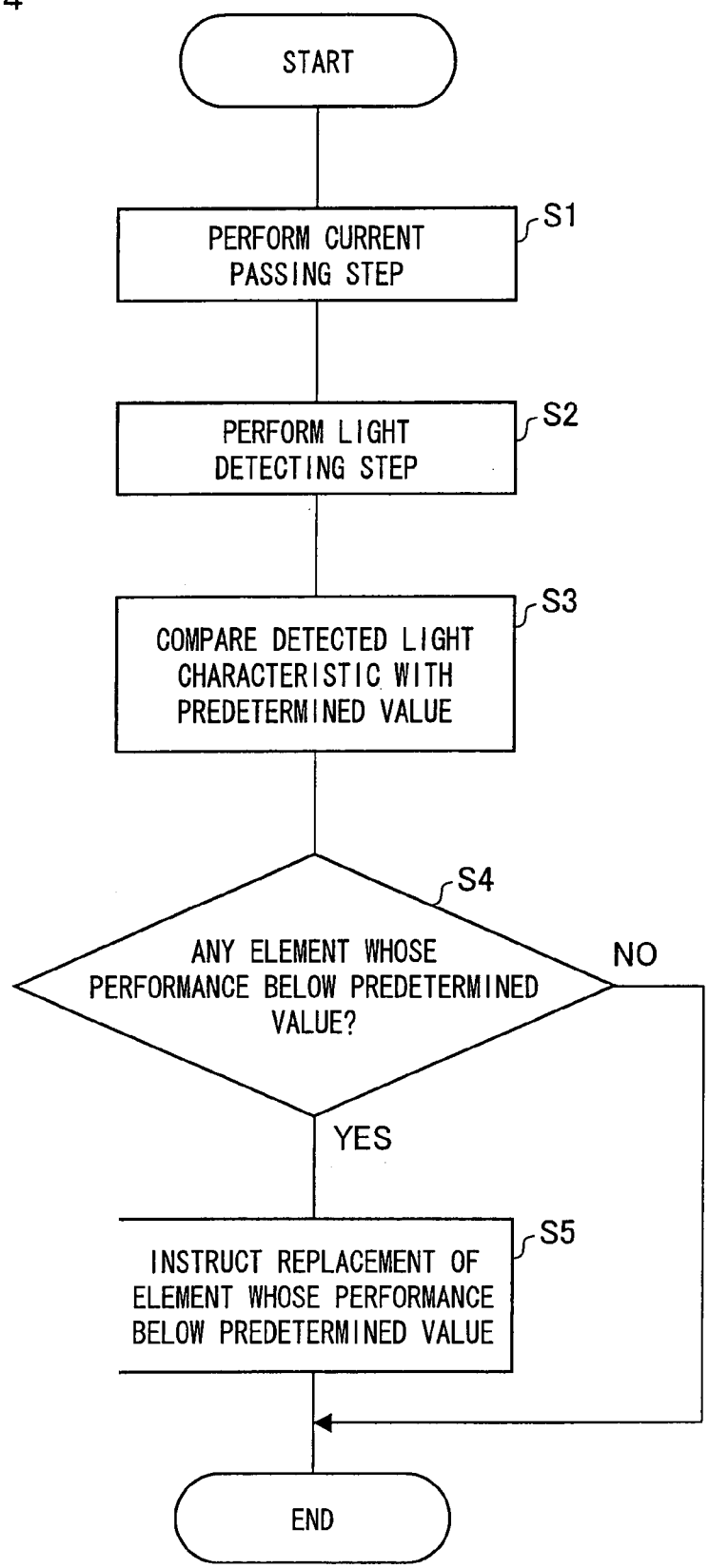
FIG. 4 is a view illustrating one example of a flow of a maintenance system according to the present embodiment.

FIG. 4 illustrates one example of a flow of the maintenance system according to the present embodiment. As illustrated in FIG. 4, in the maintenance system 100, the current passing section 11 of the evaluating apparatus 10 performs the current passing step on the solar cell module that is a target of the maintenance (Step 1, the step will be abbreviated as "S" hereinafter). Then, the light detecting section 12 of the evaluating apparatus 10 detects light characteristic of the light emitted from the solar cell due to the process in S1 (S2).

Next, the judging apparatus 20 judges, based on the result of the detection performed by the light detecting section 12, whether the solar cell module implemented on the construction has a solar cell element whose performance is below a predetermined value (S3). Then, if the judging apparatus 20 judges at S4 that the solar cell module implemented on the construction has a solar cell element whose performance is below a predetermined value ("Y"), the process goes to S5. At S5, the replacement instructing apparatus 30 communicates the terminal 50 of the replacement party via the communication network 40 so as to instruct the replacement of the solar cell element whose performance is below a predetermined value. Then, the process is terminated.

By contrast, if the judging apparatus 20 judges at S4 that the solar cell module implemented on the construction dose not have a solar cell element whose performance is below a predetermined value ("N"), the process is then terminated.

As described above, the maintenance method or maintenance system according to the present invention for solar cell do not need a large-size apparatus and can easily evaluate the solar cell in quality with a simple evaluating apparatus.

Thus, it is possible to regularly perform maintenance for a solar cell module implemented on a construction. This allows to keep the quality of the solar cell module at a certain level.

As discussed above, the conventional evaluation of the solar cell requires a large-sized apparatus. Accordingly, it has been impossible to evaluate such a solar cell module implemented on a construction such as houses etc., and to perform maintenance of such an implemented solar cell on a regular basis. By contrast, the present invention does not require a large-sized apparatus unlike the conventional art. Thus, the present invention firstly makes it possible to evaluate the performance of the solar cell implemented on a construction.

Moreover, as described above, the conventional performance evaluation using the solar simulator examines the photoelectric conversion efficiency of the whole solar cell module, and cannot perform a detailed analysis to find out a solar cell element of which position in the module has a poor conversion efficiency. Thus, if it was found out that the performance of the solar cell module was deteriorated, it would be necessary to replace all the solar cell module very wastefully.

By contrast, the present invention makes it possible to judge at one sight, by using a light characteristic as an indicator, which solar cell element is poor in performance among many solar cell elements constituting the solar cell module. Thus, it is not necessary to replace all the whole solar cell module, and only the solar cell element whose performance is poor can be replaced very economically.

The photovoltaics for generating an electric energy from affluent sun light by using the solar cell has been dramatically advanced technically in recent years to be employed as a usually-used power generating method. It is expected that photovoltaics will be prevailed as a clean energy in full scale to save the 21st century human civilization from fossil energy pollution.

The photovoltaics utilizes sun radiation energy that is exhaustless and "free". Apart from that, the photovoltaics do not have a moving part because thermal energy does not mediate the photovoltaics that uses a quantum photoelectric effect in semiconductor. Thus, the photovoltaics is regarded as a "quite, safe, and non-polluting" way to obtain electric energy. Despite of such advantages, the solar cells requires quite expensive silicon or the like of high purity, resulting in needs high cost in power generation thereof. This is one big reason why the solar cells has not been so popular yet. It has been one reason for the high cost that the expensiveness thereof makes it practically impossible to replace the whole solar cell even if its performance becomes poor, and thus there is no appropriate maintenance method for the implemented solar cell module.

However, the maintenance method and maintenance system according to the present invention for performing maintenance of the solar cell makes it possible to easily perform the maintenance of the implemented solar cell module as described above. Therefore, the present invention is applicable not only to the product inspection in the production of the solar cell module but also to the maintenance thereof, thereby contributing to popularizing the solar cell module. As such, the present invention is not only industrially applicable but also very useful for the earth environment.

Moreover, for example, the use of the present invention also makes it possible to perform the maintenance without external light (for example at night or in a dark room), by picturing the light emission from the solar cell with an infrared CCD camera and comparing the pictured image with predetermined reference data in color thickness (i.e., performing comparison process by computer-using data processing or the like). In this case, for example, it is possible to judge that it is time to replace a solar cell element when a ratio of a portion in which the emission intensity is low (e.g., white portion) exceeds a certain ratio.

It should be noted that, needless to say, various evaluating apparatuses described in the present Description are suitably applicable to the maintenance method and maintenance system, albeit the above explanation discusses the maintenance method and maintenance system using one example of the evaluating apparatus for the solar cell.

Finally, each block of the maintenance system such as the evaluating apparatus, judging apparatus, replacement instructing apparatus etc. (hereinafter these blocks are referred to as "evaluating apparatus etc.") may be constituted by hardware logic or by software logic using a CPU as described below.

Each of the evaluating apparatus etc. is provided with: a CPU (central processing unit) for executing a program for realizing a function thereof; a ROM (read only memory) for storing the program therein; a RAM (random access memory) for expanding the program therein; a storage device (recording medium), such as a memory, for storing the program and various data; and the like. The object of the present invention can be attained by supplying the evaluating apparatus etc. respectively with recording media in which software to realize the above-mentioned functions is stored in a computer-readable manner, which software is a program code (execution form program, intermediate code program, a source program) for the evaluating apparatus etc., and then causing a computer (alternatively CPU or MPU) to read out the program code from the recording medium and execute the program code.

Examples of such a recording medium include tape-type media, such as magnetic tapes, cassette tapes and the like; disk type media such as magnetic disks (such as Floppy® disks, hard disks, and the like), optical disks (such as CD-ROM, MO, MD, DVD, CD-R, and the like); a card, such as an IC card (inclusive of a memory card), and the other disks; card-type media such as IC cards (encompassing memory cards), optical cards, and the like); semiconductor memories such as mask ROM, EPROM (Erasable Programmable Read Only Memory), EEPROM (Electrically Erasable Programmable Read Only Memory), and flash ROM; and the other media.

Moreover, evaluating apparatus 10 etc. may be connected to a communication network so that the program code is supplied via the communication network. Examples of the communication network encompass: Internet, Intranet, Extranet, LAN, ISDN, VAN, CATV communication network, virtual private network, telephone lines, mobile communication network, satellite communication networks, and the like. There is no particular limitation as to communication media to constitute the communication network. For example, the communication medium may be a wired communication medium such as IEEE1394, USB, power line transmission, cable TV lines, telephone lines, ADSL lines, or a wireless communication medium such as infrared ray such as IrDA or remote control, Bluetooth®, 802.11 wireless, HDR, mobile telephone network, satellite network, terrestrial digital net, and the like communication media. The present invention can be realized in a form of computer data signal embedded in a carrier wave, by which the program code is concreted as electronic transmission.

The embodiments of the present invention are descried in more details referring to Example below. Needless to say, the present invention is not limited the following Example and can be altered in details in various ways. Furthermore, the present invention is not limited to the description of the embodiments above, and can be modified in various ways within the scope of the claims. An embodiment based on a proper combination of technical means disclosed in different embodiments is encompassed in the technical scope of the present invention.

EXAMPLE

Figure 5:
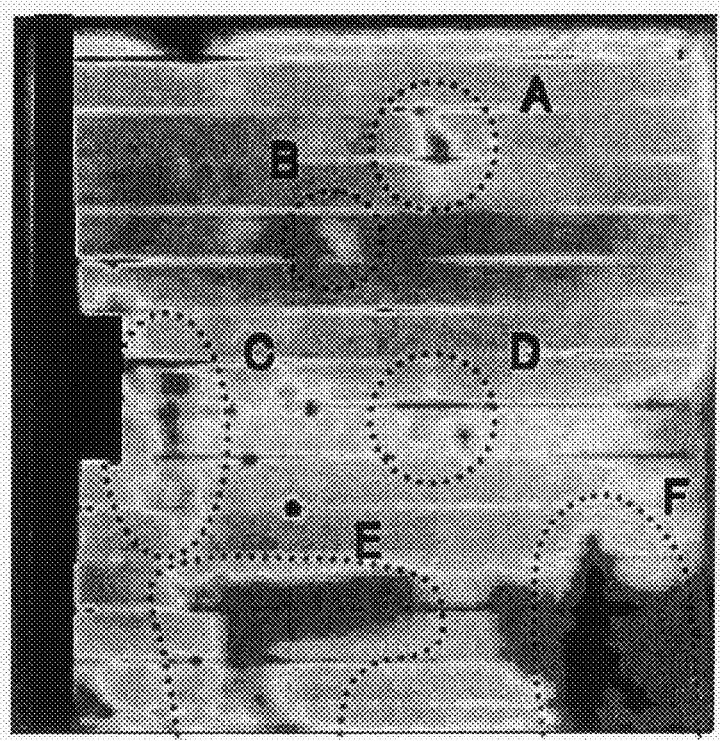
FIG. 5(a) is a view illustrating an image picturing light emission of a Si solar cell element when a current was passed therethrough.
FIG. 5(b) is a view illustrating a diffusion length of minority carriers (electrons) in the Si solar cell element when a current was passed therethrough.
Figure 5:
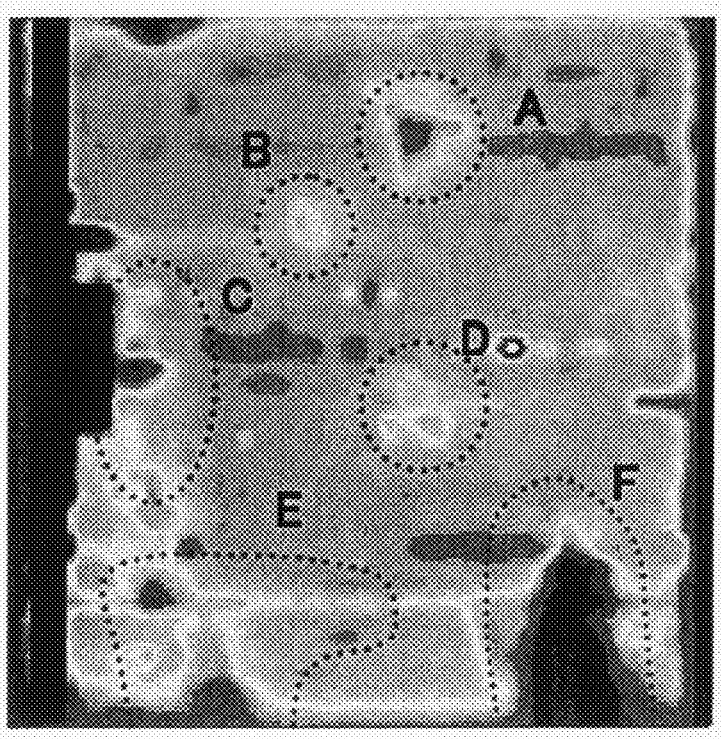

A Si solar cell element made from polycrystalline silicon semiconductor was analyzed by passing a forward current in a range of 5 to 40 mA/cm$^2$. In the present Example, an emission microscope (Hamamatsu Photonics K.K. PHEMOS-200) was used. The Si solar cell element was 1 cm×1 cm in size. Images picturing the Si solar cell element through which the current was passed are illustrated in FIGS. 5(*a*) and 5(*b*). FIG. 5(*a*) illustrates light emission from the Si solar cell element, while FIG. 5(*b*) illustrates a diffusion length of the minority carrier (electrons) in the Si solar cell element.

FIG. 5(*a*) shows that the Si solar cell element emitted strong light when the current passed therethrough. The whitish portion is a region where the light emission was strong, and the blackish portion is a region where the light emission was weak (in case of a color image, a reddish portion is the region where the light emission is strong, while a yellowish to bluish portion is the region where the light emission is weak). For example, the regions A to F circled by wavy lines are regions where the light emission was weak in FIG. 5(*a*).

In FIG. 5(*b*) illustrating the diffusion length distribution of the minority carriers, the grayish portion is a region where the diffusion length was long and whitish and blackish portions are region where the diffusion length was short (in case of a color image, a region of more reddish/orange color has a longer diffusion length; while a region of more bluish or purplish has a shorter diffusion length). For example, the regions A to F circled by wavy lines are regions where the diffusion length was short in FIG. 5(*b*).

FIGS. 5(*a*) and 5(*b*) demonstrates that the regions in which the strong light emission occurred when the current was passed through the Si solar cell element were matched with the regions in which the diffusion length was long, while the regions of weak light emission corresponded to the region having short diffusion length. This showed that the diffusion length of the minority carriers closely relates with the light characteristics such as the emission intensity of the light caused when the current was passed through the Si solar cell element. Because the diffusion length of the minority carriers are linked with a photoelectric conversion efficiency of the solar cell, the light characteristics obtained when the current was passed through the Si solar cell element was further analyzed in details.

More specifically, emission intensity (EL intensity) obtained when a current in a range of 5 to 40 mA/cm$^2$ was passed through the Si solar cell element, and spectrum characteristics of the light emitted from a solar cell module were analyzed. The result is shown in FIG. 6. The spectrum characteristics were measured using a spectrometer (JASCO Corp. M50) and germanium detector (EDINBURGH INSTRUMENT, EI-L) according to their operation manuals.

As illustrated in FIG. 6, emission of light peaked at wavelengths of 1000 nm to 1300 nm was observed when the current was passed through the Si solar cell element. The peak is being currently analyzed intensively, because it may be constituted of a plurality of spectra.

Next, a relationship between the intensity of the current to be passed through the Si solar cell and the emission intensity of the light was studied. The result is illustrated in FIG. 7(*a*). As illustrated in FIG. 7(*a*), the emission intensity of the light was increased as a greater current was passed through.

Then, the result of the analysis on the diffusion length and the emission intensity of the Si solar cell element is illustrated in FIG. 7(*b*), which shows readings of the diffusion length and the emission intensity measured while the intensity of the current to pass was changed.

As illustrated in FIG. 7(*b*), it was demonstrated that the emission intensity and the diffusion length of the minority carriers were in proportion. Because it is known that a longer diffusion length of the minority carriers improves the photoelectric conversion efficient of the solar cell, it can be understood that it was possible to evaluate the photoelectric conversion efficiency of the solar cell by passing the current through the solar cell and using the resultant emission intensity as an indicator.

Moreover, FIG. 11 is another graph illustrating the result of analysis on the relationship between the diffusion length and emission intensity of the Si solar cell element especially in the case of the currents to pass (forward currents) of 6 mA/cm$^2$, 13.5 mA/cm$^2$, and 18.7 mA/cm$^2$ among the results of FIG. 7(*b*). In FIG. 11, the left vertical axis should be referred to for the two upper straight lines, while the right vertical axis should be referred to for the lower straight line, because the emission intensity was varied in a wide range. FIG. 11 shows that the emission intensity and the diffusion length were in proportion.

Figure 8:
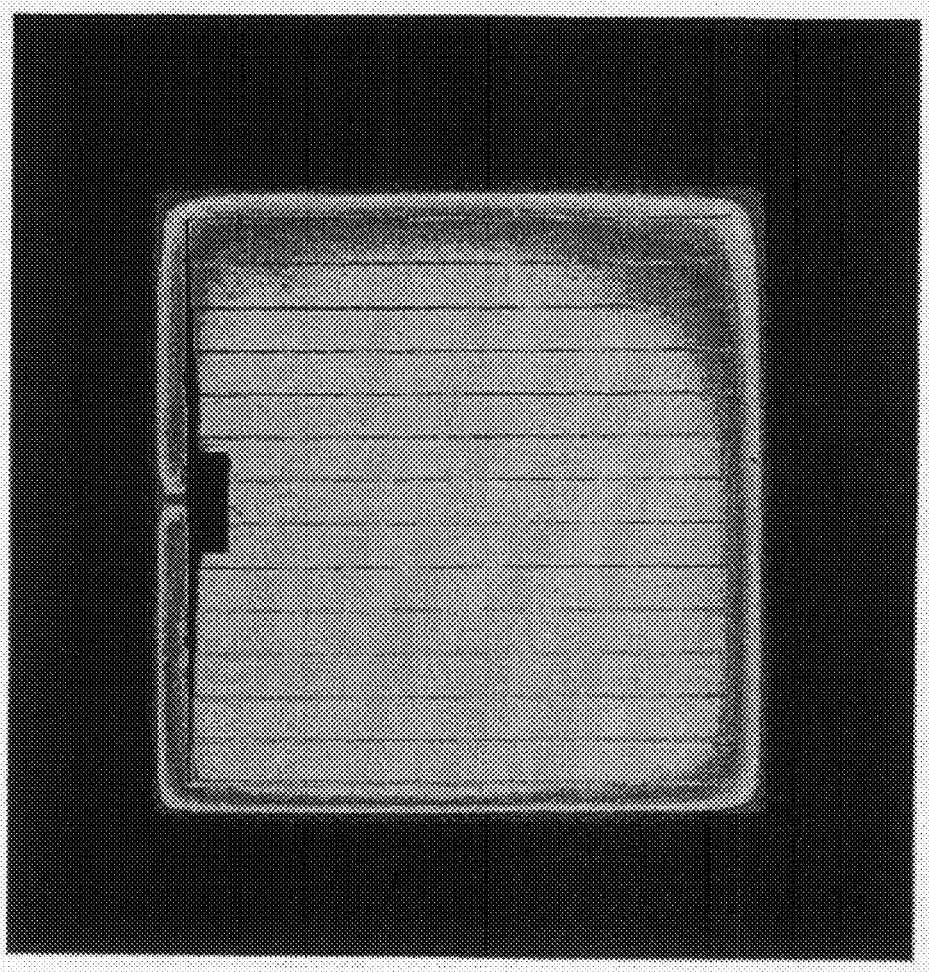
FIG. 8 is a view illustrating an image picturing light emission caused when a current was passed through a monocrystalline Si solar cell element.
Figure 9:
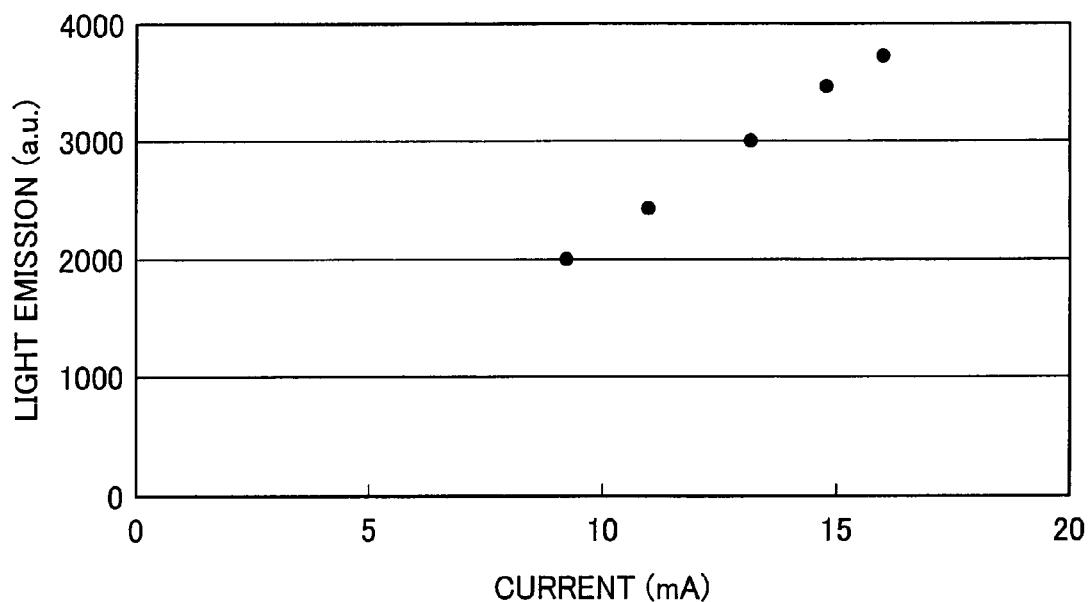
FIG. 9 is a view illustrating the result of studying emission intensity caused when the current was passed through the monocrystalline Si solar cell element.

Next, a Si solar cell element made from monocrystalline silicon semiconductor was examined to find whether it emitted light when a current was passed therethrough. The results are illustrated in FIGS. 8 and 9. FIG. 8 illustrates an image picturing the light emission of the monocrystalline Si solar cell element when the current was passed therethrough. FIG. 9 illustrates the emission intensity of the monocrystalline Si solar cell element measured when the current was passed therethrough.

FIGS. 8 and 9 demonstrates that the forward current passing the monocrystalline Si solar cell element caused light emission in the monocrystalline Si solar cell element as in the polycrystalline Si solar cell element.

Furthermore, changes in emission intensity (EL intensity) against a change in a current density were examined for the solar cell elements respectively using the monocrystalline Si solar cell element and the polycrystalline Si solar cell element. Specifically, solar cell elements of 15 cm □ made from crystalline silicon were examined in emission intensity by passing a current therethrough.

Figure 12:
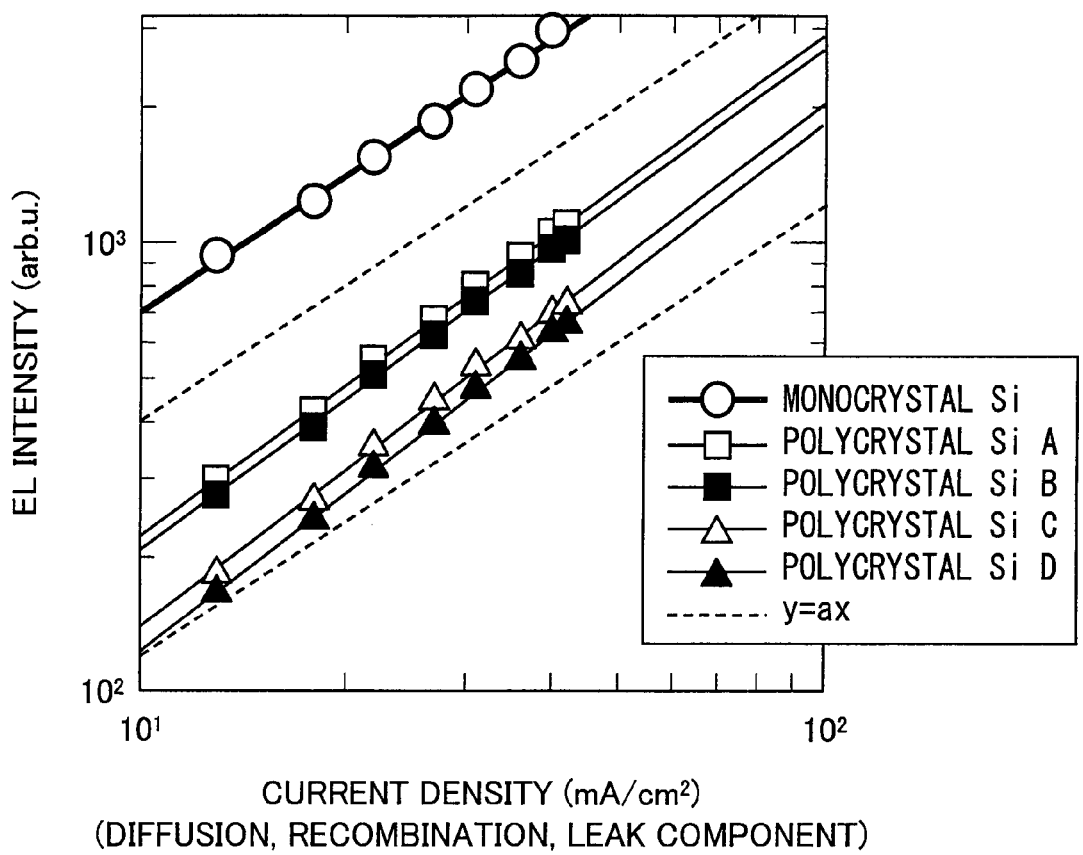
FIG. 12 is a view illustrating the result of analysis on a change in emission intensity (EL intensity) against a change in current density in solar cell elements respectively made from monocrystalline silicon and polycrystalline silicon.

The result is shown in FIG. 12. As illustrated in FIG. 12, it was demonstrated that a diffusion current was dominant in the solar cell element using the monocrystalline Si solar cell element, and a gradient thereof was substantially 1. Meanwhile, it was found that the polycrystalline Si solar cell element were influenced from other current components and a gradient thereof got closer to 1 when the EL intensity was higher. The gradients indicate the diode factor and the performance of solar cell elements are better with the gradients closer to 1

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

The method etc. according to the present invention for evaluating a solar cell is applicable not only to quality inspection in production of a solar cell module, but also to, for example, maintenance of an implemented solar cell module on a regular basis. Thus, the industrial applicability of the present invention is very wide, being not limited to inspecting apparatuses etc.

The invention claimed is:

1. A method for evaluating performance of a solar cell, comprising:
   a current passing step including forward biasing a solar cell element constituting the solar cell by passing, in a forward direction, a direct current through the solar cell element; and
   a light detecting step of detecting a light characteristic of light emitted from the solar cell element by the current passing step,
   the solar cell element being made from silicon semiconductor as its main component.

2. The method as set forth in claim 1, further comprising:
   a judging step of judging the performance by using, as an indicator, an emission intensity so as to judge the performance as good when the emission intensity is greater than a predetermined value, and to judge the performance as bad when the emission intensity is smaller than a predetermined value, the emission intensity being based on the light characteristic detected in the light detecting step.

3. The method as set forth in claim 1, further comprising:
   the judging step including
      calculating a diffusion length of minority carriers from an emission intensity, the emission intensity being based on the light characteristic detected in the light detecting step; and
   judging the performance of the solar cell by using the diffusion length as an indicator.

4. The method as set forth in claim 1, wherein an intensity of the current to be passed in the current passing step is substantially equivalent to that of an operating current of the solar cell element.

5. The method as set forth in claim 1, wherein:
   the current passing step changes the intensity of the current that is passed through the solar cell element;
   the light detecting step detects how the light characteristic of the light emitted from the solar cell element is changed in response to the change in the intensity of the current; and
   the method further comprises a step of calculating out a diode factor of the solar cell element based on the change in the intensity of the current and the change in the light characteristic.

6. The method as set forth in claim 1 wherein the silicon semiconductor is monocrystalline, polycrystalline, or amorphous.

7. The method as set forth in claim 1, wherein the light detecting step detects light of wavelengths in a range of 1000 nm to 1300 nm.

8. An apparatus for evaluating photoelectric conversion performance of a solar cell, the apparatus comprising:
   a current passing device configured to forward bias a solar cell element constituting the solar cell by passing, in a forward direction, a direct current through the solar cell element; and
   a light detecting device configured to detect a light characteristic of light emitted from the solar cell element by passing the direct current through the solar cell by the current passing device,
   the solar cell element being made from silicon semiconductor as its main component.

9. The apparatus as set forth in claim 8, further comprising:
   a judging device configured to judge the performance by using, as an indicator, an emission intensity so as to judge the performance as good when the emission intensity is greater than a predetermined value, and to judge the performance as bad when the emission intensity is smaller than a predetermined value, the emission intensity being based on the light characteristic detected by the light detecting device.

10. The apparatus as set forth in claim 8, further comprising:
    a judging device configured to calculate a diffusion length of minority carriers from an emission intensity, and judge the performance of the solar cell by using the diffusion length as an indicator, the emission intensity being based on the light characteristic detected by the light detecting device.

11. The apparatus as set forth in claim 8, wherein:
    the current passing device is configured to change the intensity of the current that is passed through the solar cell element;
    the light detecting device is configured to detect how the light characteristic of the light emitted from the solar cell element is changed in response to the change in the intensity of the current; and
    the apparatus further comprises a calculating device configured to calculate out a diode factor of the solar cell element based on the change in the intensity of the current and the change in the light characteristic.

12. A method for performing maintenance of a solar cell, the method comprising:
    an apparatus as set forth in claim 8 evaluating the solar cell that is implemented on a construction;
    a judging apparatus judging, based on a result of the evaluation of the solar cell, whether the solar cell has a solar cell element whose performance is below a predetermined value; and
    a replacement instructing apparatus instructing, via a communication network, a replacement part for the solar cell element, to replace the solar cell element whose performance is below the predetermined value.

13. A system for performing maintenance of a solar cell, comprising:
    an apparatus as set forth in claim 8;

a judging apparatus for judging, based on a result of the evaluation performed by the apparatus, whether the solar cell has a solar cell element whose performance is below a predetermined value; and a replacement instructing apparatus for instructing, via a communication network, a replacement part for the solar cell element, to replace the solar cell element whose performance is below the predetermined value.

14. A method for producing a solar cell, comprising, as one step thereof, a method as set forth in claim 1.

* * * * *